United States Patent [19]
Bulan et al.

[11] Patent Number: 5,366,597
[45] Date of Patent: Nov. 22, 1994

[54] PROCESS FOR THE PREPARATION OF PERFLUOROBUTYLSULPHONYL FLUORIDE

[75] Inventors: Andreas Bulan, Langenfeld; Rainer Weber, Odenthal, both of Germany

[73] Assignee: Bayer AG, Leverkusen, Germany

[21] Appl. No.: 67,585

[22] Filed: May 27, 1993

[30] Foreign Application Priority Data

Jun. 5, 1992 [DE] Germany ............ 4218562

[51] Int. Cl.$^5$ ............ C07C 309/80
[52] U.S. Cl. ............ 204/59 F; 204/157.7
[58] Field of Search ............ 204/157.7, 59 F

[56] References Cited

U.S. PATENT DOCUMENTS

| | | | |
|---|---|---|---|
| 3,625,963 | 12/1971 | Capitant et al. | 260/243 A |
| 3,883,450 | 5/1975 | Burg et al. | 260/2 R |
| 3,919,057 | 11/1975 | Plattner et al. | 204/59 F |
| 3,951,762 | 4/1976 | Voss et al. | 204/59 F |
| 3,960,764 | 6/1976 | Bernard et al. | 252/429 R |

FOREIGN PATENT DOCUMENTS 2201649  7/1993  Germany .

OTHER PUBLICATIONS

Orbit Abstract of De-A-1912738 (Oct. 1, 1970).
Official Gazette publication of U.S. Pat. No. 3,623,963 (Nov. 30, 1971).

*Primary Examiner*—John Niebling
*Assistant Examiner*—Edna Wong
*Attorney, Agent, or Firm*—Connolly & Hutz

[57] ABSTRACT

The invention relates to a process for the preparation of perfluorobutylsulphonyl fluoride by electrochemical fluorination of butylsulphonyl fluoride, tetrahydrothiophene-1,1-dioxide (sulpholane), 2,5-dihydrothiophene-1,1-dioxide (sulpholene) or mixtures of these in hydrogen fluoride.

12 Claims, 1 Drawing Sheet

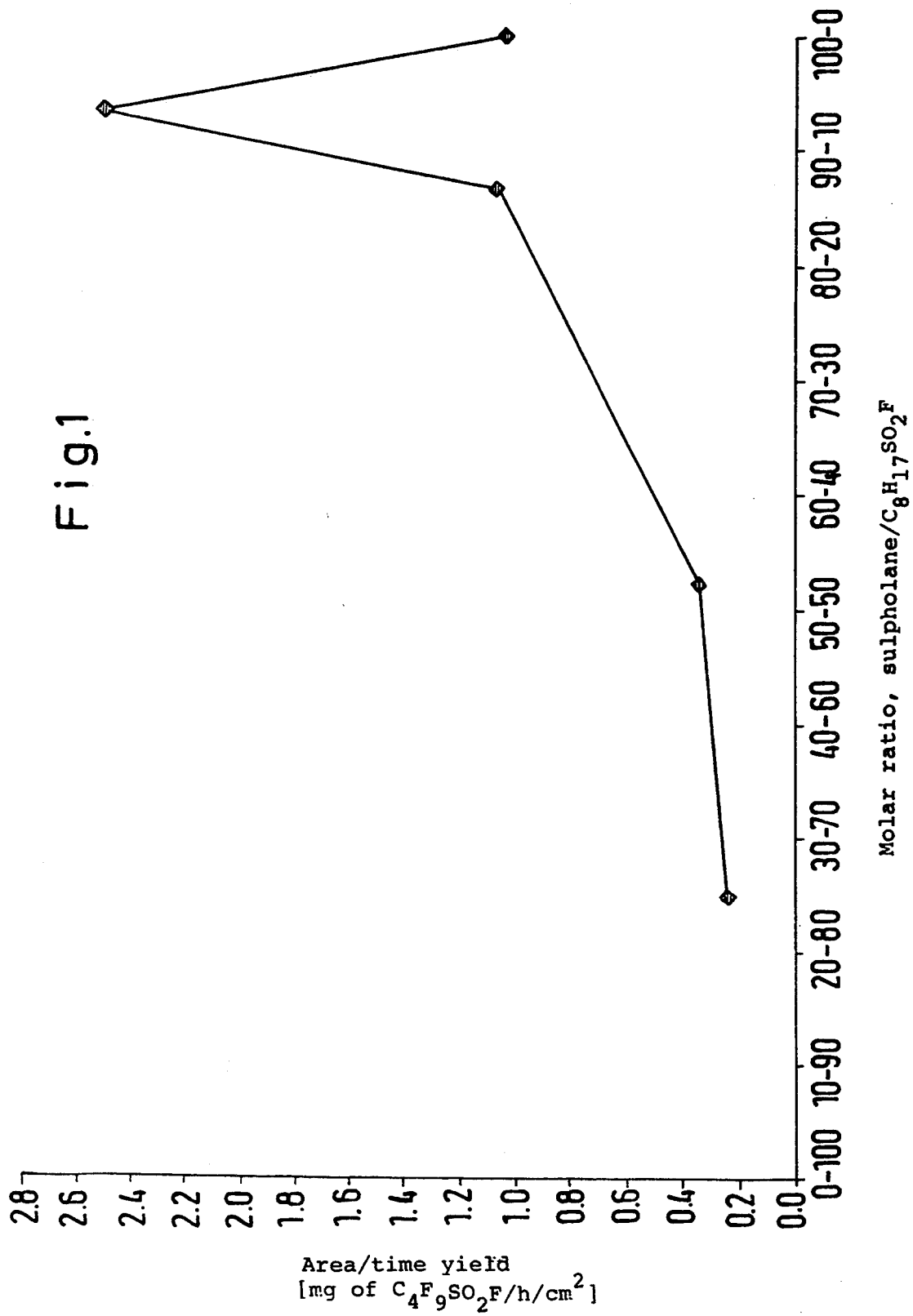

PROCESS FOR THE PREPARATION OF PERFLUOROBUTYLSULPHONYL FLUORIDE

The invention relates to a process for the preparation of perfluorobutylsulphonyl fluoride by electrochemical fluorination of butylsulphonyl fluoride, tetrahydrothiophene-1,1-dioxide (sulpholane), 2,5-dihydrothiophene-1,1-dioxide (sulpholene) or mixtures of these in hydrogen fluoride.

Perfluorobutylsulphonyl fluoride is a valuable intermediate for the preparation of e.g. perfluorobutanesulphonic acid and its derivatives. Perfluorobutanesulphonic acid is used, for example, as a catalyst in isomerisation, alkylation and polymerization reactions (DE-A 24 45 561 and DE-A 21 41 600).

Furthermore, according to DE-A 22 39 817, perfluorobutanesulphonic acid is used for the preparation of bisperfluorobutylsulphonimides and their derivatives, which may be used as surfactants and, like perfluorobutanesulphonic acid, as a catalyst.

Perfluorobutylsulphonyl fluoride is usually prepared, according to DE-C 19 12 738, by electrochemical fluorination of butylsulphonyl fluoride, sulpholane or sulpholene or mixtures of these compounds. The disadvantage of this process is that perfluorobutylsulphonyl fluoride may only be obtained with low area/time yields. The area/time yield describes how much product is produced per unit of time per geometric anode area.

DE-C 22 01 649 describes a process by which perfluorobutylsulphonyl fluoride with high material yields may be produced, when a mixture of 5 parts by weight of octylsulphonyl fluoride and 1 part by weight of sulpholene is electrochemically fluorinated. The disadvantage of this process is that, despite the high material yields, a low area/time yield is produced.

Therefore, the object was to provide a process, which did not possess the disadvantages mentioned, thus with which perfluorobutylsulphonyl fluoride may be prepared in high material yields and at the same time in high area/time yields.

Surprisingly, the object could be achieved by electrochemically fluorinating butylsulphonyl fluoride, sulpholane, sulpholene or mixtures thereof together with octylsulphonyl fluoride, wherein the molar ratio of butylsulphonyl fluoride, sulpholane or sulpholene or mixtures thereof to octylsulphonyl fluoride is 86:14 to 99:1.

The present invention provides a process for the preparation of perfluorobutylsulphonyl fluoride by electrochemical fluorination of butylsulphonyl fluoride, sulpholane, sulpholene or mixtures thereof in anhydrous hydrogen fluoride in the presence of octylsulphonyl fluoride which is characterized in that the molar ratio of butylsulphonyl fluoride, sulpholane, sulpholene or mixtures thereof to octylsulphonyl fluoride is 86:14 to 99:1.

When performing the process according to the invention, perfluorobutylsulphonyl fluoride is obtained with high area/time yields, which are clearly greater than those which were achieved using the known processes.

The electrolysis cells used for electrofluorination consist of nickel or another material which does not corrode in the presence of hydrogen fluoride such as, for example, perfluorinated plastics. The anodes consist of nickel and the cathodes of nickel or iron. The distance between the electrodes is 2 to 5 mm. The temperature of the electrolyte is generally between 0° and 20° C., but it may also be between 20° and 50° C., as described in DE-A 24 42 106.

Details of the construction and operating conditions of the electrolysis cells are summarized in Chem.-Ing.-Tech. 58, 31–38 (1986) and the references cited there.

The process according to the invention is preferably performed in such a way that hydrogen fluoride and 2% by weight based on the hydrogen fluoride used, of the starting material to be fluorinated are initially placed in an electrolysis cell.

The starting material to be fluorinated consists of a mixture of octylsulphonyl fluoride and of sulpholane, sulpholene, butylsulphonyl fluoride or mixtures thereof.

A constant voltage of 4–6 V, preferably 5 V, is applied across the cell and the starting material to be fluorinated is continuously metered into the cell in the requisite stoichiometry.

Reaction equations:
Octylsulphonyl fluoride:

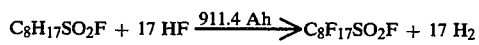

Sulpholane:

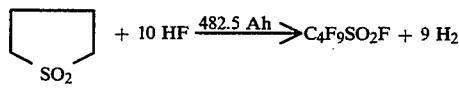

Sulpholene:

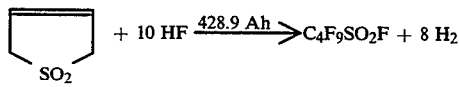

Butylsulphonyl fluoride:

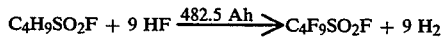

If mixtures of octylsulphonyl fluoride, sulpholane, sulpholene or butylsulphonyl fluoride are electrochemically fluorinated, then the amounts to be added are calculated from the reaction equation for the particular substance.

The hydrogen fluoride consumed is replaced batchwise. The resulting mixture of perfluorobutyl- and perfluorooctyl-sulphonyl fluoride is removed batch-wise from the cell at specific intervals of time.

The invention is intended to be explained in more detail using the following examples:

Example 1 (Prior art according to DE-C 22 01 649)

35 kg of hydrogen fluoride and a mixture of octylsulphonyl fluoride and sulpholane in a ratio of 5:1 by weight were electrochemically fluorinated in an electrolysis cell with an anode area of 12390 cm$^2$, wherein 11.9 kg of octylsulphonyl fluoride and 2.38 kg of sulpholene were converted using a charge of 50796 Ah. The temperature of the electrolyte was 9° C.

In the test, which was run over a period of 1033.4 hours, a C$_8$F$_{17}$SO$_2$F material yield of 34.5% of theory and a C$_4$F$_9$SO$_2$F material yield of 50.9% of theory was produced. The area/time yields were 0.820 mg of C$_8$F$_{17}$SO$_2$F per hour per square centimeter and 0.238 mg of C$_4$F$_9$SO$_2$F per hour per square centimeter. An average current density of 3.97 mA.cm$^{-1}$ was produced.

Example 2 (Electrofluorination of sulpholane; comparison)

28 kg of anhydrous hydrogen fluoride and 500 g of sulpholane were initially placed in an electrolysis cell with an anode area of 8000 cm$^2$ and a voltage of 5 V was applied across the cell. Sulpholane was continuously metered into the cell in amounts corresponding to the reaction stoichiometry (see page 3). 100.7 kg of sulpholane were converted using a charge of 396324 Ah.

During the reaction time of 11365 hours, there was an average current density of 4.36 mA/cm$^2$. The material yield of perfluorobutylsulphonyl fluoride was on average 37.8% and the average area/time yield was 1.032 mg of C$_4$F$_9$SO$_2$F per hour per square centimeter.

Example 3 (Electrofluorination of sulpholane (9 parts by wt.) with octylsulphonyl fluoride (1 part by wt.); according to the invention)

19 kg of anhydrous hydrogen fluoride and 350 g of a mixture of sulpholane and octylsulphonyl fluoride in a ratio of 9:1 by weight were initially placed in an electrolysis cell with an anode area of 4750 cm$^2$ and a voltage of 5 V was applied across the cell. A mixture was continuously metered into the cell in amounts corresponding to the reaction stoichiometry.

A mixture of 50.44 kg of octylsulphonyl fluoride and 5.6 kg of sulpholane was converted using a charge of 233029 Ah.

During the reaction time of 5320 hours, the average current density was 11.5 mA/cm$^2$. The average material yield of perfluorobutylsulphonyl fluoride was 50.6%, that of perfluorooctylsulphonyl fluoride 56.5%. The average area/time yield was 2.5 mg of C$_4$F$_9$SO$_2$F per hour per square centimeter and 0.3158 mg of C$_8$F$_{17}$SO$_2$F per hour per square centimeter.

Example 4 (Electrofluorination of sulpholane (8 parts by wt.) and octylsulphonyl fluoride (2 parts by wt.); comparison)

16.5 kg of anhydrous hydrogen fluoride and 350 g of a mixture of sulpholane and octylsulphonyl fluoride in a ratio of 8:2 by weight were initially placed in an electrolysis cell with an anode area of 4750 cm$^2$ and a voltage of 5 V was applied across the cell. A mixture was continuously metered into the cell in amounts corresponding to the reaction stoichiometry.

A mixture of 11.6 kg of octylsulphonyl fluoride and 2.9 kg of sulpholane was converted using a charge of 59933 Ah.

The average area/time yield was 1.06 mg C$_4$F$_9$SO$_2$F per hour per square centimeter and 0.375 mg of C$_8$F$_{17}$SO$_2$F per hour per square centimeter.

Example 5 (Electrofluorination of sulpholane (4 parts by wt.) and octylsulphonyl fluoride (6 parts by wt.); comparison)

27 kg of anhydrous hydrogen fluoride and 540 g of the mixture of sulpholane and octylsulphonyl fluoride in a ratio of 4:6 by weight were initially placed in an electrolysis cell with an anode area of 9750 cm$^2$. A mixture was continuously metered into the cell in amounts corresponding to the reaction stoichiometry.

A mixture of 31.2 kg of octylsulphonyl fluoride and 20.8 kg of sulpholane was converted using a charge of 231123 Ah.

During the reaction time of 8748 hours there was an average current density of 2.71 mA/cm$^2$. The average material yield of perfluorobutylsulphonyl fluoride was 54.9%, that of perfluorooctylsulphonyl fluoride was 35%. The average area/time yield was 0.3363 mg of C$_4$F$_9$SO$_2$F per hour per square centimeter and 0.328 mg of C$_8$F$_{17}$SO$_2$F per hour per square centimeter.

The results of the tests are summarized in Table 1 and FIG. 1.

As can be seen from Table 1 and FIG. 1, much higher area/time yields were obtained using the process according to the invention (i.e., Example 3).

TABLE 1

| Example | 1 | 2 | 3 | 4 | 5 |
|---|---|---|---|---|---|
| Molar ratio of | | | | | |
| C$_8$H$_{17}$SO$_2$F | 75.15 | — | 6.37 | 13.27 | 47.87 |
| Sulpholane | 24.85 | 100 | 93.63 | 86.73 | 52.13 |
| Material yield (% of theory) | | | | | |
| C$_8$F$_{17}$SO$_2$F | 34.5 | — | 56.5 | 54.3 | 35 |
| C$_4$F$_9$SO$_2$F | 50.9 | 37.8 | 50.6 | 39.2 | 54.9 |
| Area/time yields [mg of perfluorinated product · h$^{-1}$ · cm$^{-2}$]$^{1)}$ | | | | | |
| C$_8$F$_{17}$SO$_2$F | 0.820 | — | 0.315 | 0.375 | 0.328 |
| C$_4$F$_9$SO$_2$F | 0.238 | 1.03 | 2.5 | 1.06 | 0.3363 |
| Average current density [mA · cm$^{-2}$]$^{1)}$ | 3.97 | 4.36 | 11.5 | 5.5 | 2.71 |
| Reaction time in hours | 1033.4 | 11365 | 5320 | 2302 | 8748 |
| Anodes area [cm$^2$] | 12390 | 8000 | 4750 | 4750 | 9750 |

$^{1)}$The data given as cm$^2$ refers to the geometric area of the anode.

What is claimed is:

1. A process for the preparation of perfluorobutylsulphonyl fluoride by electrochemical fluorination of a mixture of butylsulphonyl fluoride in anhydrous hydrogen fluoride and octylsulphonyl fluoride, wherein the molar ratio of butylsulphonyl fluoride to octylsulphonyl fluoride is 87:13 to 99:1.

2. A process for the preparation of perfluorobutylsulphonyl fluoride by electrochemical fluorination of a mixture of sulpholane in anhydrous hydrogen fluoride and octylsulphonyl fluoride, wherein the molar ratio of sulpholane to octylsulphonyl fluoride is 87:13 to 99:1.

3. A process according to claim 2, wherein the molar ratio of sulpholane to octylsulphonyl fluoride is about 94:6 to 99:1.

4. A process for the preparation of perfluorobutylsulphonyl fluoride by electrochemical fluorination of a mixture of sulpholene in anhydrous hydrogen fluoride and octylsulphonyl fluoride, wherein the molar ratio of sulpholene to octylsulphonyl fluoride is 87:13 to 99:1.

5. A process for the preparation of perfluorobutylsulphonyl fluoride by electrochemical fluorination of one of the following mixtures and octylsulphonyl fluoride in anhydrous hydrogen fluoride: a) butylsulphonyl fluoride and sulpholane; b) butylsulphonyl fluoride and sulpholene; c) butylsulphonyl fluoride, sulpholane and sulpholene and d) sulpholane and sulpholene, wherein the molar ratio of the mixture of octylsulphonyl fluoride is 87:13 to 99:1.

6. The process of claim 1, wherein the molar ratio of butylsulphonyl fluoride to octylsulphonyl fluoride is about 94:6 to 99:1.

7. The process of claim 4, wherein the molar ratio of sulpholene to octylsulphonyl fluoride is about 94:6 to 99:1.

8. The process of claim 5, wherein the molar ratio of the mixture of octylsulphonyl fluoride is about 94:6 to 99.1.

9. The process of claim 1, wherein the molar ratio of butylsulphonyl fluoride to octylsulphonyl fluoride is about 94:6.

10. The process of claim 2, wherein the molar ratio of sulpholane to octylsulphonyl fluoride is about 94:6.

11. The process of claim 4, wherein the molar ratio of sulpholene to octylsulphonyl fluoride is about 94:6.

12. The process of claim 5, wherein the molar ratio of the mixture of octylsulphonyl fluoride is about 94:6.

* * * * *

UNITED STATES PATENT AND TRADEMARK OFFICE
CERTIFICATE OF CORRECTION

PATENT NO. : 5,366,597
DATED : November 22, 1994
INVENTOR(S) : Bulan et al.

It is certified that error appears in the above-identified patent and that said Letters Patent is hereby corrected as shown below:

Col. 5, line 10, (claim 5, line 8), the words "mixture of octylsulphonyl" should read --mixture to octylsulphonyl--.

Signed and Sealed this

Twenty-second Day of August, 1995

Attest:

BRUCE LEHMAN

Attesting Officer

Commissioner of Patents and Trademarks